(12) United States Patent
Rohde et al.

(10) Patent No.: US 8,216,452 B2
(45) Date of Patent: *Jul. 10, 2012

(54) DIALYSIS SYSTEM INCLUDING MULTI-HEATER POWER COORDINATION

(75) Inventors: Justin Rohde, Des Plaines, IL (US); William W. Han, Long Grove, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/030,909

(22) Filed: Feb. 18, 2011

(65) Prior Publication Data

US 2011/0132841 A1    Jun. 9, 2011

Related U.S. Application Data

(63) Continuation of application No. 12/031,605, filed on Feb. 14, 2008, now Pat. No. 7,892,423.

(51) Int. Cl.
*B01D 61/30* (2006.01)
*B01D 61/32* (2006.01)
*B01D 21/30* (2006.01)
*H05B 1/02* (2006.01)

(52) U.S. Cl. ........ 210/149; 210/134; 210/138; 210/141; 210/142; 210/143; 210/321.71; 210/482; 210/483; 210/485; 210/492; 604/6.13

(58) Field of Classification Search .......... 210/85, 210/134, 138, 139, 140, 141, 142, 143, 149, 210/175, 177, 252, 257.1, 321.71; 604/6.13; 236/1 C, 1 E, 46 R, 74 R, 91 E, 101 C
See application file for complete search history.

(56) References Cited

U.S. PATENT DOCUMENTS

| | | |
|---|---|---|
| 3,563,381 A | 2/1971 | Edelson et al. |
| 3,685,680 A | 8/1972 | Tenckhoff et al. |
| 3,744,636 A | 7/1973 | Commarmot |
| 3,814,249 A | 6/1974 | Eaton |
| 3,878,095 A | 4/1975 | Frasier et al. |
| 3,915,802 A | 10/1975 | Kominek |
| 4,060,485 A | 11/1977 | Eaton |
| 4,067,803 A | 1/1978 | Quentin |
| 4,209,402 A | 6/1980 | Gentles |
| 4,348,280 A | 9/1982 | George et al. |
| 4,360,323 A | 11/1982 | Anderson |
| 4,655,941 A | 4/1987 | Suzuki |
| 4,664,891 A | 5/1987 | Cosentino et al. |

(Continued)

FOREIGN PATENT DOCUMENTS

WO    96/40318    12/1996

OTHER PUBLICATIONS

International Search Report for corresponding International Application PCT/US2009/031809 dated Oct. 19, 2009.

(Continued)

*Primary Examiner* — John Kim
(74) *Attorney, Agent, or Firm* — K&L Gates LLP

(57) ABSTRACT

A dialysis system includes a first fluid heater, a second fluid heater, a supplemental power source and a logic implementer. The logic implementer is configured to use the supplemental power source such that when the first and second heaters are powered simultaneously, a collective current draw does not exceed a maximum allowable current draw of a branch power source powering the system.

9 Claims, 9 Drawing Sheets

U.S. PATENT DOCUMENTS

| | | | |
|---|---|---|---|
| 4,734,198 A | 3/1988 | Harm et al. |
| 4,955,508 A | 9/1990 | Capanna et al. |
| 4,976,683 A | 12/1990 | Gauthier et al. |
| 5,032,265 A | 7/1991 | Jha et al. |
| 5,122,516 A | 6/1992 | Watanabe et al. |
| 5,256,371 A | 10/1993 | Pippert |
| 5,274,434 A | 12/1993 | Morioka et al. |
| 5,295,505 A | 3/1994 | Polaschegg et al. |
| 5,318,750 A | 6/1994 | Lascombes |
| 5,326,473 A | 7/1994 | Lascombes et al. |
| 5,385,564 A | 1/1995 | Slater et al. |
| 5,498,338 A | 3/1996 | Kruger et al. |
| 5,540,842 A | 7/1996 | Aoyama et al. |
| 5,591,344 A | 1/1997 | Kenley et al. |
| 5,616,248 A | 4/1997 | Schal |
| 5,866,880 A | 2/1999 | Seitz et al. |
| 5,895,578 A | 4/1999 | Simard et al. |
| 5,948,251 A | 9/1999 | Brugger |
| 6,146,536 A | 11/2000 | Twardowski |
| 6,251,279 B1 | 6/2001 | Peterson et al. |
| 6,274,103 B1 | 8/2001 | Taylor |
| 6,348,162 B1 | 2/2002 | Ash |
| 6,426,056 B2 | 7/2002 | Taylor |
| 6,464,977 B2 | 10/2002 | Kai et al. |
| 6,489,301 B1 | 12/2002 | Kobira et al. |
| 6,595,944 B2 | 7/2003 | Balschat et al. |
| 6,623,709 B2 | 9/2003 | Taylor |
| 6,673,376 B1 | 1/2004 | Knerr et al. |
| 6,685,831 B2 | 2/2004 | Donig et al. |
| 6,745,903 B2 | 6/2004 | Grandics |
| 6,787,032 B2 | 9/2004 | Kurome et al. |
| 6,861,033 B2 | 3/2005 | Mullins et al. |
| 6,902,670 B2 | 6/2005 | Ho |
| 6,908,546 B2 | 6/2005 | Smith |
| 6,923,987 B2 | 8/2005 | Kai et al. |
| 6,986,872 B2 | 1/2006 | Taylor |
| 7,045,061 B2 | 5/2006 | Nishimura et al. |
| 7,077,956 B2 | 7/2006 | Rovatti |
| 7,208,092 B2 | 4/2007 | Micheli |
| 7,250,619 B2 | 7/2007 | Taylor et al. |
| 2003/0135250 A1 | 7/2003 | Lauman et al. |
| 2003/0220605 A1 | 11/2003 | Bowman et al. |
| 2007/0278155 A1 | 12/2007 | Lo et al. |
| 2009/0008331 A1 | 1/2009 | Wilt et al. |

OTHER PUBLICATIONS

Written Opinion for corresponding International Application PCT/US2009/031809 dated Oct. 19, 2009.

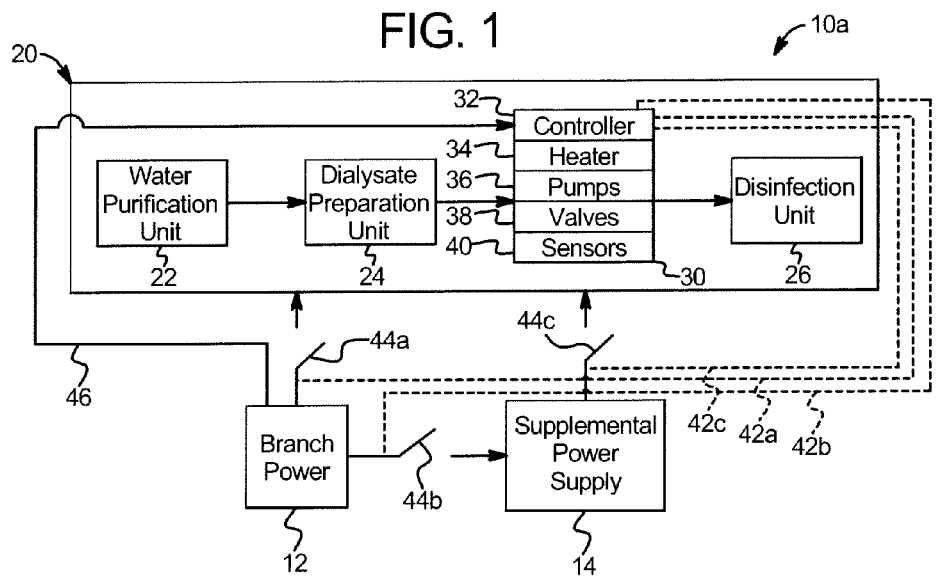
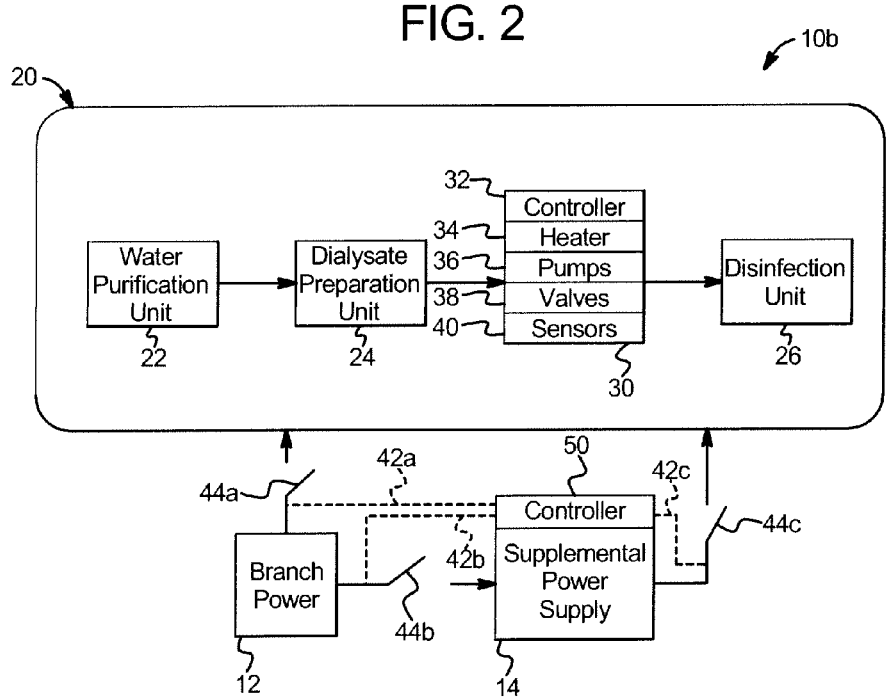

DIALYSIS SYSTEM INCLUDING MULTI-HEATER POWER COORDINATION

PRIORITY

This application claims priority to and the benefit as a continuation application of U.S. patent application entitled, "Dialysis System Including Multi-Heater Power Coordination", Ser. No. 12/031,605, filed Feb. 14, 2008, now U.S. Pat. No. 7,892,423, the entire contents of which are incorporated herein by reference and relied upon.

BACKGROUND

The present disclosure relates generally to medical fluid systems and more particularly to dialysis systems that can be used in a patient's home.

It is expected that the power requirements during a typical usage cycle of a home dialysis device will vary significantly. During therapy, which can last for two to eight hours, energy usage is expected to be particularly high. The dialysis delivery and water purification systems require significant amounts of energy to run heaters, pumps, valves, etc. Similarly, disinfection equipment and processes that are operated at the end of therapy can also require large amounts of electricity. The instantaneous amount of energy required during those states may exceed the wattage which can be supplied by a standard home electrical branch (e.g., 15 ampere, 110/120 volt, or equivalent). The patient's branch power may need to be upgraded to a higher operating current and/or voltage to run a therapy.

It is desirable not to have to upgrade the patient's electrical system.

SUMMARY

The system of the present disclosure is a medical fluid system, such as a dialysis system, which can be used in a patient's home. The medical fluid system in one embodiment generates dialysis fluid. The process begins by purifying water. The purified water is delivered to the dialysis machine, which adds concentrates to the purified water to create dialysate. The apparatus therefore includes a water purification system placed on the front end of the dialysis machine. The system generates dialysate online, that is, it generates the medical fluid as it is needed as opposed to being pre-generated and stored in supply bags. As discussed, the need to upgrade the electrical system of a patient's home to handle both dialysate preparation and dialysate delivery could provide an impediment to adoption of the therapy. The present system accordingly provides a supplemental power supply, which is connected in parallel with the patient's line or branch power. During therapy or other high-energy demand operation, the supplemental power is discharged into the system to prevent the total power draw from the load or branch from exceeding its load rating. After therapy is completed or otherwise when the current requirement of the dialysis system drops, the supplemental power supply draws power from the branch circuit. For example, there may be sixteen to twenty-two hours per day that the equipment is not in use. The supplemental source during this time replenishes its power reserve for the next dialysis treatment.

In one embodiment, both the branch and the supplemental power devices supply power during therapy to the dialysis hardware. In various implementations illustrated below the branch and the supplemental power devices: (i) operate in parallel to supply power to each of the medical fluid components requiring power; or (ii) are dedicated individually to one or more of the medical fluid components requiring power (e.g., branch supplies power to each of the medical fluid components requiring power except for the dialysate preparation unit which is powered via the supplemental power source). After therapy power from both sources to the medical fluid hardware is shut down (or reduced to a hibernation level), and the line or branch power source recharges the supplemental power source.

The supplemental power source can be one of several different types, each of which offers different benefits and drawbacks. In one embodiment, the supplemental power source is an electrochemical battery or batteries, e.g., which uses a rechargeable chemistry such as Lithium-Ion, Lithium-Ion-Polymer, Lithium-Ion-Phosphate, Lithium-Sulfur, Lithium-Nano-Titanate, Nickel-Metal-Hydride, Nickel-Cadmium, Nickel-Iron, Nickel-Zinc, Lead-acid, and rechargeable-alkaline cells. Each of the chemistries is capable of storing sufficient amounts of energy in a reasonably sized package to fit the medical fluid application. These cells are rechargeable but are limited typically to several hundred to thousands of charge/discharge cycles before the cells have to be replaced. Depending on the chemistry of the cells, the cells can also present environmental issues.

The supplemental power source can alternatively be one or more capacitor, such as an ultracapacitor (sometimes called a supercapacitor). Ultracapacitors have faster discharge rates than the electrochemical batteries but offer the benefit of survival across millions of charge/discharge cycles without performance degradation. Moreover, recent advancements in the capacitor field have achieved energy densities in excess of 300 W(h)/kg, approximately twice the density of a Lithium-Ion cell. Moreover, the high rate of discharge for ultracapacitor is not necessarily a drawback because the high discharge rate would allow a capacitor of a given energy density to supply more instantaneous energy to the system than a battery of equivalent energy density.

A third option is to convert water during off-therapy hours into pressurized hydrogen using an electrolysis reaction. During therapy, the hydrogen is oxidized in a fuel cell to produce electrical current for use by the device. The electrolysis reaction is very energy inefficient, however, the resulting hydrogen generation is highly flammable and is therefore stored safely and at relatively low pressures in one preferred embodiment.

For online dialysis, two heaters may be provided, one for a dialysate preparation unit and one for a dialysate delivery unit. Powering the heaters at both times may exceed the peak current rating for the branch or line power (assuming branch or line power is powering both heaters). The heaters are each powered via a duty cycle using pulse width modulation, which for each heater applies maximum power to the heater for a first period of time and no power to the heater for a second period of time. The first time relative to the second time sets the duty cycle (e.g., fifty percent duty cycle requires full power for half the time and no power for half the time).

The present system includes a logic implementer or controller configured to, as much as possible, apply power to only one of the heaters at any given time. For example, the logic implementer or controller can be configured such that if the first heater needs power, the logic implementer looks to see if the second heater is currently being powered. If not, the logic implementer causes power to be supplied to the first heater. If so, the logic implementer keeps checking to see if the second heater is currently being powered and causes power to be supplied to the first heater as soon as the second heater is no longer being powered. The logic implementer is further configured such that if the second heater needs power, the logic implementer looks to see if the first heater is currently being powered. If not, the logic implementer causes power to be supplied to the second heater. If so, the logic implementer keeps checking to see if the first heater is currently being powered and causes power to be supplied to the second heater as soon as the first heater is no longer being powered.

In another example, the logic implementer or controller powers the first heater for a first predetermined duration and then powers the second heater for a second predetermined duration, the durations dependent upon the respective required duty cycles of the two heaters. If the collective duty cycles are less than one-hundred percent, the logic implementer or controller is further configured to apply no power to either heater for a predetermined period of time after one or both of the first and second predetermined power durations. In one embodiment, the logic implementer or controller attempts to space apart the powering of the two heaters as much as possible.

The above algorithms are best suited for first and second heaters that are sized and configured to each operate at less than fifty percent duty cycle. When the combined duty cycle of the two heaters is greater than one-hundred percent, the logic implementer is configured to minimize the amount of time of overlapping powering of the first and second heaters as much as possible. To do so, a second heater is powered at the instant power is removed from a first heater. The logic implementer then waits as long as possible (according to the duty cycle of the first heater) to re-power the first heater. The second heater is powered for as long as needed according to its duty cycle. This procedure is repeated, eliminating power overlap as much as possible.

The supplemental power source discussed above can be used to prevent the dual heaters from drawing too much current. In one embodiment, the branch or line power and the supplemental power source are split to each power one of the heaters. In another embodiment, one of the branch or line power alone is used to power both heaters when the heaters do not have to be powered at the same time. The second power source is called upon whenever both heaters are being powered, either to power one of the heaters or to add to a collective power source that can provide the needed current draw of both heaters.

It is accordingly an advantage of the present disclosure to provide a medical fluid system having a relatively large power requirement, and which can be used in a patient's home without having to upgrade the patient's line power.

It is another advantage of the present disclosure to provide a medical fluid system having a supplemental power source configured to power one or more electrical component of the system.

It is a further advantage of the present disclosure to provide a medical fluid system that separates the powering of dual heaters used in the system to minimize total power draw.

Additional features and advantages are described herein, and will be apparent from, the following Detailed Description and the figures.

BRIEF DESCRIPTION OF THE FIGURES

FIG. 1 is a schematic view of one embodiment of a medical fluid or dialysis system having a line or branch power source and a supplemental power source.

FIG. 2 is a schematic view of another embodiment of a medical fluid or dialysis system having a line or branch power source and a supplemental power source.

DETAILED DESCRIPTION

Figure 3:
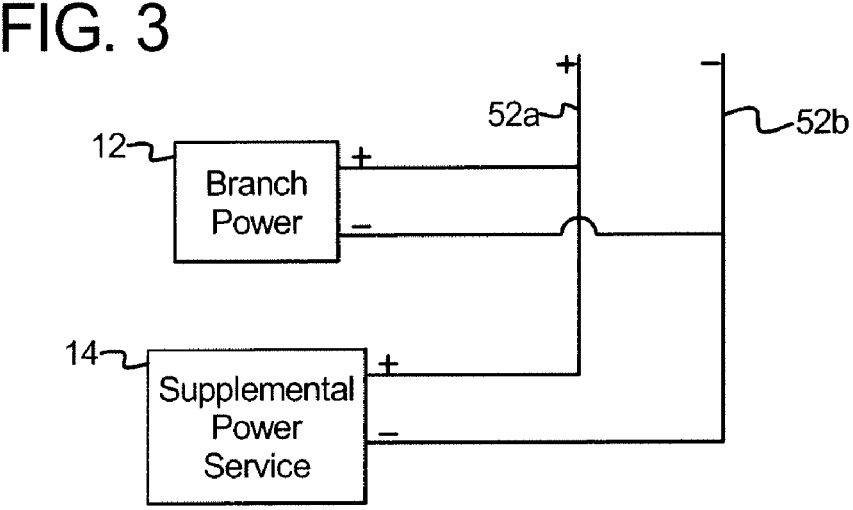
FIG. 3 is a schematic view illustrating one mode of operating both the line and branch power sources with the medical fluid or dialysis system.

Medical Fluid System Having Supplemental Power Supply

Referring now to the drawings and in particular to FIG. 1, system 10a illustrates one embodiment of a medical fluid system employing a supplemental power supply or source. System 10a illustrates a dialysis system, and in particular an online dialysis system, which produces dialysate or dialysis fluid online (mixing dialysate components at the time of therapy as opposed to the use of a premixed, bagged dialysate). The dialysis system can be a peritoneal dialysis ("PD") system, a hemodialysis ("HD") system, a hemofiltration ("HF") system, a hemodiafiltration ("HDF") system and a continuous renal replacement therapy ("CRRT") system. System 10a includes apparatus 12 for receiving line or branch power, such as 120 VAC or 240 VAC residential or commercial power. Apparatus 12 includes a plug and/or a cord and any needed power regulation apparatus, such as a transformer, analog to digital converter and any fusing or other desired circuit protection.

System 10a includes a supplemental power source or supply 14. Supplemental power source 14 includes wiring or circuit board traces that connect to branch power apparatus 12, such that branch power apparatus 12 can deliver power to supplemental power source 14. Supplemental power supply 14 includes an apparatus capable of receiving power from branch power apparatus 12, storing such power and delivering the power when needed to the medical fluid or dialysis apparatus described herein. The apparatus can be one of several different types, each of which offers different benefits and drawbacks. In one embodiment, supplemental power source 14 includes an electrochemical battery or batteries, e.g., which uses a rechargeable chemistry such as Lithium-Ion, Lithium-Ion-Polymer, Lithium-Ion-Phosphate, Lithium-Sulfur, Lithium-Nano-Titanate, Nickel-Metal-Hydride, Nickel-Cadmium, Nickel-iron, Nickel-Zinc, Lead-acid, and rechargeable-alkaline cells. Each of the chemistries is capable of storing sufficient amounts of energy in a reasonably sized package to fit the medical fluid application. These cells are rechargeable but are limited typically to several hundred to thousands of charge/discharge cycles before the cells have to be replaced. Depending on the chemistry of the cells, the cells can also present environmental issues.

Supplemental power source 14 is alternatively one or more capacitor, such as an ultracapacitor (sometimes called a supercapacitor). Ultracapacitors have higher faster discharge rates than the electrochemical batteries but offer the benefit of survival across millions of charge/discharge cycles without performance degradation. Moreover, recent advancements in the capacitor field have achieved energy densities in excess of 300 W(h)/kg, approximately twice the density of a Lithium-Ion cell. A third option is to convert water during off-therapy hours into pressurized hydrogen using an electrolysis reaction. During therapy, the hydrogen is oxidized in a fuel cell to produce electrical current for use by the device.

As discussed, in one embodiment, branch power 12 and supplemental power source 14 power a dialysis machine 20. In the illustrated embodiment, dialysis machine 20 includes a water purification unit 22, a dialysate preparation unit 24, a dialysate delivery unit 30 and a disinfection unit 26. One example of a water purification unit is discussed in copending application Ser. No. 11/937,232, entitled, "Water Distillation System For Home Dialysis", filed Nov. 8, 2007, assigned to the assignee of the present application, the entire contents of which are disclosed herein by reference. One example of a dialysate preparation unit is discussed in U.S. Pat. No. 5,274,434 ("the '434 patent"), entitled "Method And Apparatus For Kidney Dialysis, assigned to the assignee of the present application, the relevant contents which are incorporated herein expressly by reference.

Disinfection unit 26 can be part of the dialysate generation and delivery units, that is, use the same pumps, valves and heater as the other units. Disinfection unit 26 in one embodiment uses the machine heater to heat water within the dialysate circuit to a temperature sufficient to neutralize infectious agents in the flow path. Alternatively, disinfection unit 26 includes a port for accepting a disinfecting chemical is used with or without heat in the fluid circuit. Disinfection unit 26 further alternatively generates the chemical, e.g., ozone, which passes atmospheric oxygen through a live electric arc. The ozone is pumped through the dialysate path, sterilizing the path. To reiterate, disinfection unit 26 can be a separate module, or can use existing components, which are part of one or more of dialysate preparation unit 24 and dialysate delivery unit 30.

One example of a dialysate delivery unit 30 is described in the '434 patent above, the relevant portions of which are incorporated expressly herein by reference. In general, dialysate delivery unit 30 includes a controller 32, a dialysate heater 34, one or more pump 36 to pump dialysate (and potentially additionally to pump blood for a blood dialysis treatment), valves 38 and electrically/pneumatically controlled sensors 40, such as pressure sensors, temperature sensors, conductivity sensors, air detection sensors, blood leak detection sensors, etc.

Controller 32 in one embodiment includes a plurality of controllers, each including processing and memory. Controller 32 can for example include a master or supervisory processor that controls a plurality of delegate processors, each of which are dedicated to various functions of dialysis system 20. Controller 32 can also include redundant processing, such as a safety processor which ensures that each of the other processors is performing its function correctly.

Controller 32 can control any one or more of water purification unit 22, dialysate preparation unit 24 and disinfection unit 26 in addition to controlling heater 34, pump 36, valves 38 and sensors 40. In the embodiment illustrated in FIG. 1, controller 32 of dialysate system 20 is further configured to control the switching associated with branch power 12 and supplemental power supply 14 via electrical or signal lines 42a to 42c, which extend respectively to a branch power switch 44a connecting branch power 12 to dialysis machine 20, switch 44b connecting branch power 12 to supplemental power supply 14 and a third switch 44c connecting supplemental power supply 14 to dialysis instrument 20.

Controller 32 via signal line 42a selectively opens or closes switch 44a to selectively allow branch power from branch power supply 12 to dialysis instrument 20. Controller 32 via signal line 42b controls switch 44b to allow power selectively from branch power supply 12 to charge supplemental power supply 14. Controller 32 uses signal line 42c to selectively open and close switch 44c to allow supplemental power supply 14 to supply power to dialysis instrument 20.

In the embodiment illustrated in FIG. 1, branch power supply 12 powers controller 32 via a power line 46 independent of switches 44a and 44c. In this manner, controller 32 can be powered at anytime via power line 46 regardless of the state of switches 44 (referring collectively to switches 44a to 44c). At least a small amount of power can therefore be supplied to controller 32 of dialysis instrument 20 at any given time. There may however be instances in system 10a when no power is supplied to the instrument, e.g., controller 32 runs on on-board battery power.

Referring now to FIG. 2, alternative system 10b having branch power 12 and supplemental power supply 14 is illustrated. Here, each of the components of dialysis system 20 including water purification unit 22, dialysate preparation unit 24, dialysate delivery unit 30, disinfection unit 26, branch power apparatus 12 and supplemental power supply 14 are the same as described above for system 10a. System 10b is different however in that a separate controller 50 is provided with supplemental power supply 14 for controlling switches 44 via signal lines 42 (referring collectively to signal lies 42a to 42c) to allow (i) branch power to selectively supply power to dialysis instrument 20 and/or supplemental power supply 14 and (ii) supplemental power supply 14 to selectively supply power to dialysis instrument 20.

Dialysis preparation unit 30 still includes controller or control scheme 32 as described above for controlling any one or more of dialysis delivery unit 30, water purification unit 22, dialysate preparation unit 24 and disinfection unit 26. Separate power line 46 from branch power supply 12 to controller 32 is not needed in system 10b. There may be instances in system 10b when no power is supplied to the instrument.

In one embodiment, supplemental power supply 14 powers controller 50. Controller 50 can be shutdown at any time dialysis instrument 20 is not functioning and no power is supplied from branch power supply 12 to supplemental power supply 14. Controller 50 is powered and active however even if branch power 12, not supplemental power supply 14 is supplying power to dialysis instrument 20 currently.

Regardless of whether system 10a or 10b is used, it is contemplated to use a plurality of different switch states for switches 44 to allow power to be delivered to dialysis instrument 20 (via on or both supplies 12 and 14) or for branch power supply 12 to supplemental power supply 14. In one switch state, switch 44b from branch power supply 12 to supplemental power supply 14 is open, while switches 44a and 44c from branch power 12 and supplemental power supply 14, respectively, to dialysis instrument 20 are closed. Here, both power supplies are powering dialysis instrument 20 and accordingly splitting the overall power load, so that the overall system 10 (referring collectively to system 10a or 10b) can operate with existing branch or power in the patient's home. Different embodiments for splitting the power load between branch power 12 and supplemental power supply 14 are illustrated below.

It is contemplated to use only one of branch power 12 and supplemental power supply 14 when powering dialysis instrument 20, for example, when the power load is relatively low. For example, there may be a water purification phase in which water purification unit 22, dialysate preparation unit 24, dialysate delivery unit 30 and disinfection unit 26 have to be powered, so that both supplies 12 and 14 are needed. There may be a different time during treatment, in which only dialysate preparation unit 24 and dialysate delivery unit 30 are powered. Here only one of the units, e.g., branch power supply 12, needs to power dialysis instrument 20. Here, switch 44a is closed, while switch 44c is open. Switch 44b can be opened or closed, such that branch power may not or may, respectively, charge supplemental power supply 14.

Still further alternatively, in the state of therapy in which not as much power needs to be delivered, supplemental power supply 14 can be powering the entire dialysis instrument 20, while branch power 12 is either not used or is charging supplemental power supply 14. Here, switch 44c is closed, switch 44a is open and switch 44b is open or closed depending on whether branch power 12 is charging power supply 14.

In another switch state, when therapy is completed, no power is supplied from either branch power 12 or supplemental power supply 14 to instrument 20 (except perhaps a hibernation load amount of power for example from branch power 12 to controller 32 via separate power line 46). Here, branch power 12 can recharge supplemental power supply 14 before the next therapy begins. For example, after eight hours of therapy using both supplies 12 and 14, system 10 (referring collectively to systems 10a and 10b) can use the remaining hours of the day, or a portion thereof, to cause branch power 12 to charge supplemental power supply 14. In such case, switches 44a and 44c to dialysis instrument 20 are opened, while switch 44b from branch power 12 to supplemental power supply 14 is closed. If supplemental power supply 14 becomes fully charged before therapy begins, switch 44b can be opened to stop any further charging of supplemental power supply 14.

Referring now to FIGS. 3 to 6, various embodiments for splitting power between branch power 12 and supplemental power source 14 are illustrated. In FIG. 3, branch power 12 and supplemental power source 14 are wired into a single pair of power lines 52a and 52b to dialysis instrument 20. Here, the single pair of power lines 52a and 52b powers instrument 20 regardless of the current demand. The lines however accommodate any current demand without having to upgrade branch power 12.

Figure 4:
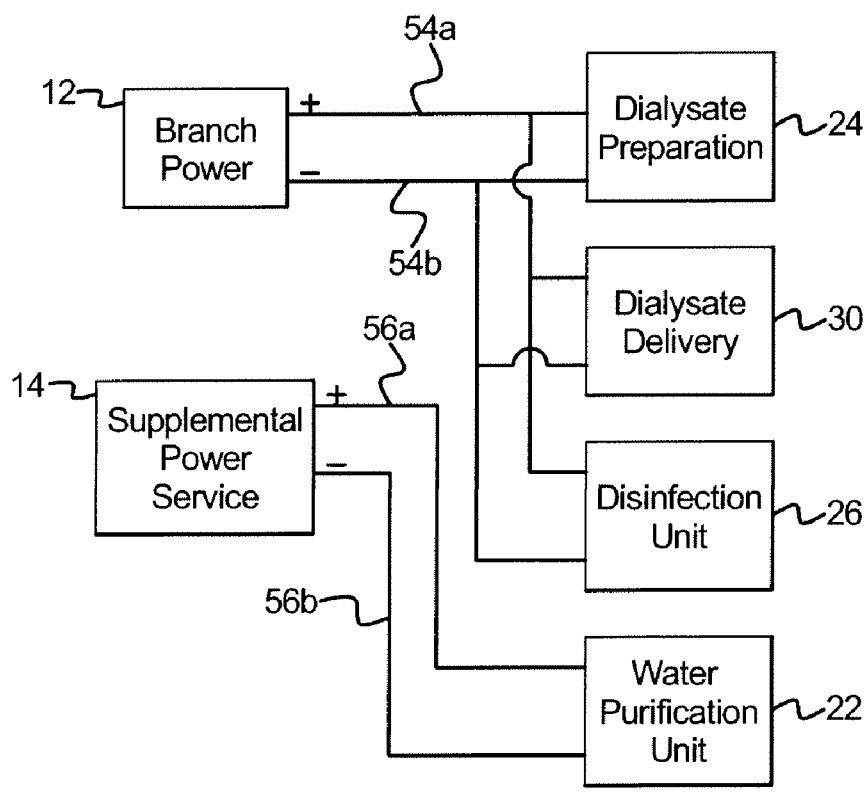
FIG. 4 is a schematic view illustrating another mode of operating both the line and branch power sources with the medical fluid or dialysis system.

Referring now to FIG. 4, a second embodiment for splitting power between branch power 12 and supplemental power source 14 is illustrated. Here, branch power 12 is dedicated to dialysate preparation unit 24, dialysate delivery unit 30 and disinfection until 26 via branch power lines 54a and 54b. Supplemental power source 12 is dedicated to powering water purification unit 22 via dedicated supplemental power lines 56a and 56b. It is expected that water purification unit 22 will consume a relatively high amount of power when it is needed. Supplemental power source 14 is dedicated to this load. It is also expected that disinfection unit 26 will operate at a different time than dialysate preparation unit 24 is operated.

Further, only a portion of dialysate delivery unit 30, e.g., the dialysate pump or pumps and associated valves, may need to be powered while disinfection unit 26 is running (e.g., to pump hot disinfecting water or solution from disinfection unit 26 through the dialysate side of instrument 20 to clean the dialysis instrument. The blood side of a blood treating dialysis treatment may be likewise disinfected or be a disposable unit that does not need to be cleaned. Accordingly, the three units 24, 26 and 30 connected to branch power 12 in FIG. 4 will likely not be operating at least a peak power draw at the same time.

Figure 5:
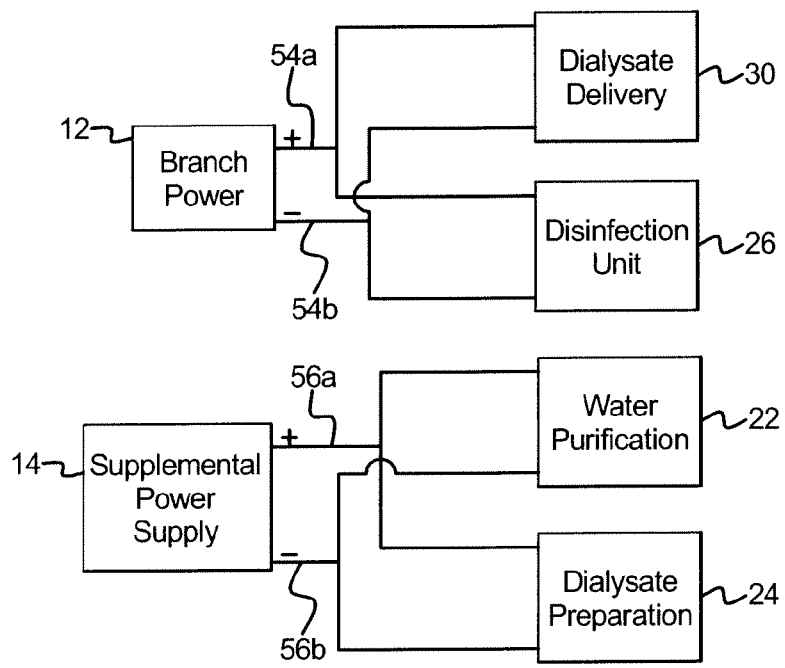
FIG. 5 is a schematic view illustrating a further mode of operating both the line and branch power sources with the medical fluid or dialysis system.

Referring now to FIG. 5, a further alternative splitting of branch power 12 and supplemental power supply 14 is illustrated. Here, branch power 12 via branch power lines 54a and 54b powers dialysate delivery unit 30 and disinfection unit 26. Supplemental power supply 14 via supplemental power lines 56a and 56b powers water purification unit 22 and dialysate preparation unit 24. Water purification unit 22 and dialysate preparation unit 24 in one embodiment operate in tandem to produce dialysate or dialysis fluid for use. In an alternative embodiment, water purification unit 22 operates prior to therapy to produce purified water. Dialysate preparation unit 24 draws the purified water during treatment to prepare the final dialysate solution. Dialysate delivery unit 30 operates during dialysis to perform treatment. Disinfection unit 26 is used at the end of treatment as discussed above to clean dialysis instrument 20. Dialysate delivery unit 30 is likely not powered fully while disinfection unit 26 is operating as discussed above.

Figure 6:
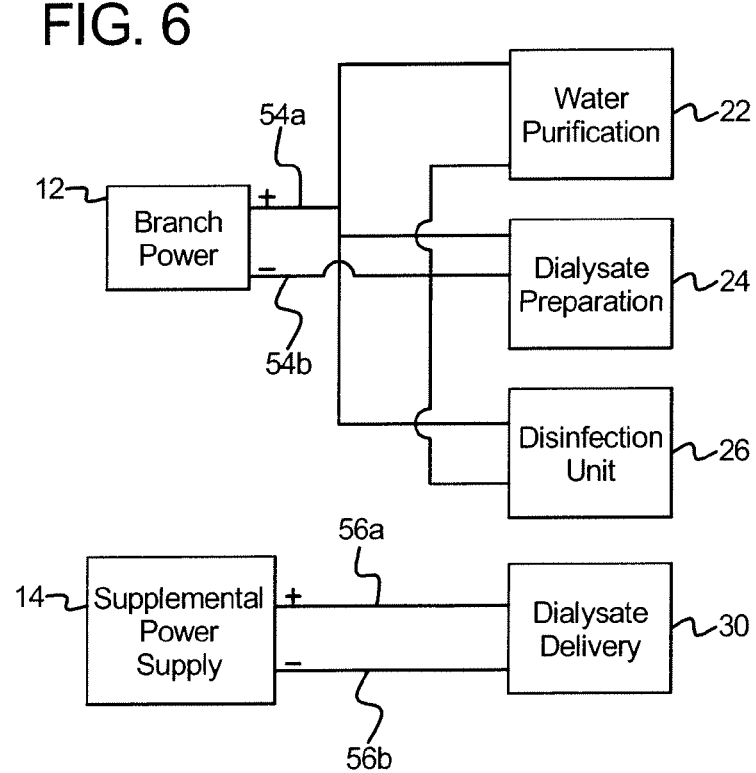
FIG. 6 is a schematic view illustrating still another mode of operating both the line and branch power sources with the medical fluid or dialysis system.

Referring now to FIG. 6, yet another alternative embodiment for splitting power between branch power 12 and supplemental power supply 14 is illustrated. Here, branch power 12 via branch power lines 54a and 54b powers each of water purification unit 22, dialysate preparation unit 24 and disinfection unit 26. Supplemental power supply 14 via power lines 56a and 56b is dedicated to powering dialysate delivery unit 30. Here, it is likely that water purification unit 22 and dialysate preparation unit 24 will be operated at a different time than disinfection unit 26. Dialysate delivery unit 30 may be powered during a portion or all the time that water purification unit 22, dialysate preparation unit 24 and disinfection unit 26 are powered. Accordingly, it is believed that the partition of power via FIG. 6 is also an efficient way to split the overall power requirement of system 10.

Multi-Heater Duty Cycle Coordination

It is contemplated that both the water purification unit 22 and dialysate delivery unit 30 will each include a dedicated heater. Heaters are typically one of the larger power consuming components of a medical delivery system, including dialysis systems. The heaters can vary from a batch type variety, which typically uses resistive plate heating, to an inline variety, which can use resistive plate heating or inductive heating (see, e.g., application Ser. No. 11/773,903, entitled "Dialysis Fluid Heating Systems", filed Jul. 6, 2007, assigned to the assignee of the present application).

The following methods and algorithms partition the individual duty cycles of the dual heaters as much as possible to prevent a combined power draw by both heaters from exceeding a current rating of the patient's line or branch power. It is contemplated to use the following methods alone or in combination with the supplemental power supply systems 10 above to minimize total power draw and to prevent an upgrade of the patient's line or branch power.

Heaters, such as plate heaters, are powered typically via pulse with modulation ("PWM"). PWM either supplies full power or one-hundred percent for a certain period of time and then no power or zero percent power for another period of time. This allows associated electronics to operate without variable resistors or other type of analog control device to apportion full power into some needed percentage. For example, a heater using PWM provides a duty cycle of fifty percent by applying full power or one-hundred percent for half the time the heater is operated and no power or zero percent for the other half of the time that the heater is operated. In the following examples, the heater systems and algorithms attempt to modify the PWM sequence to power a first heater during a second heater's zero percent power or no power duration and power the second heater during the first heater's zero power or no power duration.

Figure 7A:
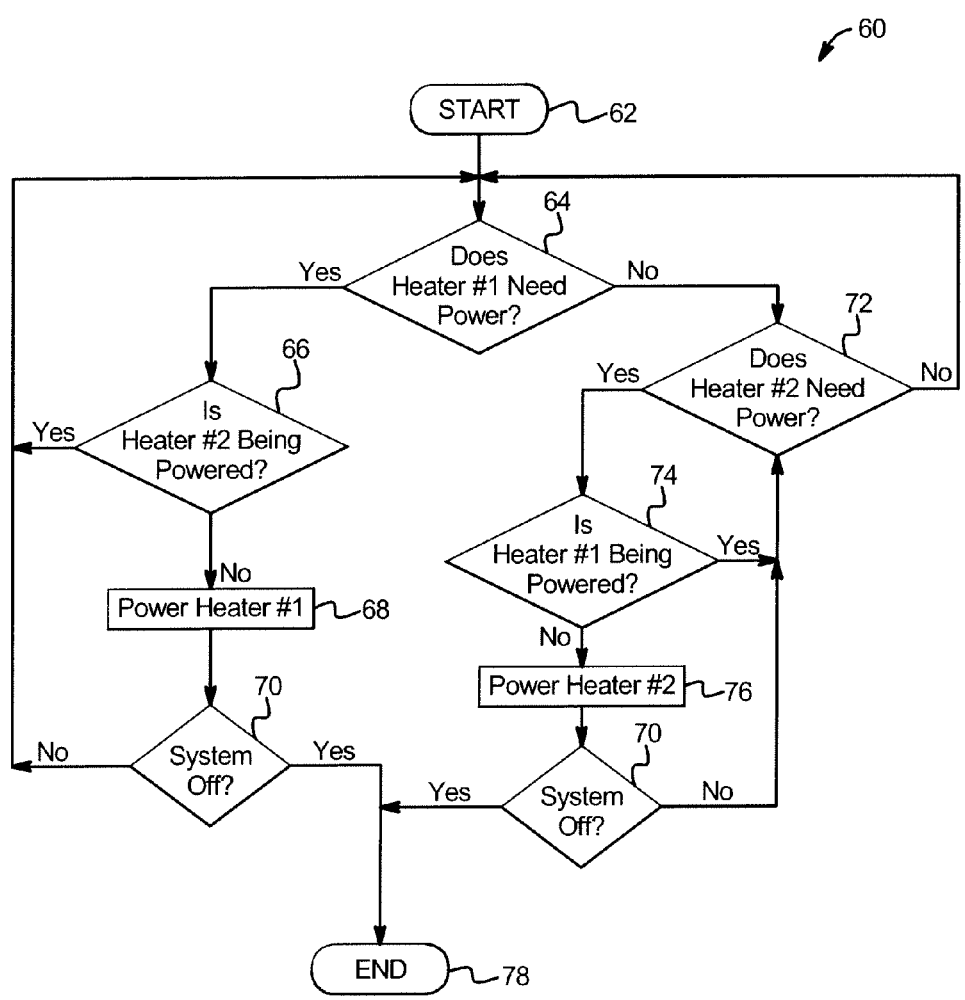
FIG. 7A is a logic flow diagram illustrating one method or algorithm for powering dual heaters of a medical fluid system.

Method or algorithm 60 of FIG. 7A starts at oval 62 and at diamond 64 determines whether a first heater (heater No. 1) needs power. If so, algorithm 60 next determines whether a second heater (heater No. 2) is currently being powered at diamond 66. If the second heater is not being powered as determined at diamond 66, method 60 causes the first heater to be powered according to its PWM sequence as seen at block 68. If the fluid heating has not yet been completed, as determined at diamond 70, and if the second heater is not being powered as determined in connection with diamond 66, method or algorithm 60 makes a return loop to diamond 64 to determine whether the first heater still needs to be powered. The loop just described is continued until either the system finished heating fluid, as determined at diamond 70, or the first heater no longer needs power, as determined in connection with diamond 64.

If the first heater does not need power, as determined at diamond 64, method or algorithm 60 determines whether the second heater needs power at diamond 72. If the second heater does need power, a loop back to diamond 64 is created, which continues until either the first or second heaters needs power. It should be appreciated that during this loop neither heater is powered, which is a time of relatively little current draw, which is desirable for reducing the overall load on the associated residential or commercial power supply.

When the second heater does need power, as determined in connection with diamond 72, method or algorithm 60 determines whether or not the first heater is currently being powered at diamond 74. If the first heater is being powered as determined at diamond 74, algorithm 60 returns to diamond 72 to determine whether the second heater still needs power. The loop between diamond 72 and diamond 74 is continued until the second heater needs power and the first heater is no longer being powered. Thus it should be seen that method or algorithm 60 prevents the two heaters from being heated at the same time and only powers each heater for as long as it needs to be powered.

When the first heater is no longer being powered and the second heater needs power, as determined in connection diamonds 72 and 74, method or algorithm 60 causes heater number two to be powered according to its PWM sequence as seen in block 76. If the system has not completed its fluid heating, as determined at diamond 70, a loop back to diamond 72 is created, which is repeated until either the second heater no longer needs power or the system has completed its fluid heating. If neither heater no longer requires power, as determined at diamond 70, method or algorithm 60 ends as seen at oval 78.

Figure 7B:
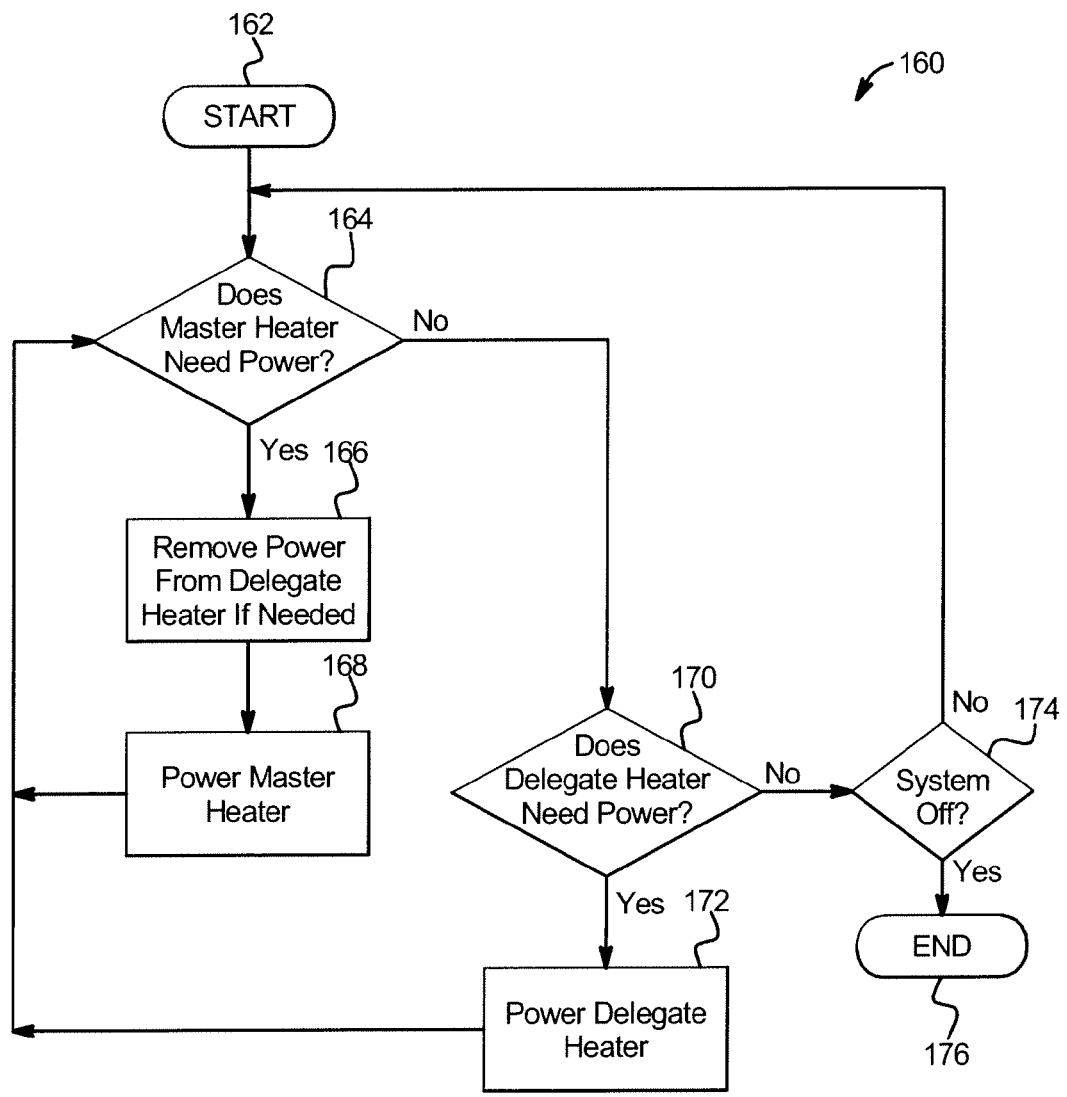
FIG. 7B is a logic flow diagram illustrating another method or algorithm for powering dual heaters of a medical fluid system according to a master/delegate relationship.

FIG. 7B illustrates a method similar to that of method 60 of FIG. 7A. Here however, method 160 allows for the first and second heaters to operate in a master/delegate relationship. Here, the master heater is used for any needs of the dialysate preparation unit 24, the disinfection unit 26 and the delivery unit 30 (e.g., the PD/HD/HDF/CRRT machine), which is connected to the patient and delivers fluid at a precise temperature. The delegate heater is assigned to water purification unit 22, for which precise control is less critical. It should be appreciated that a separate disinfection unit 26 can be provided for each of PD/HD/HDF/CRRT machine 30 and the water purification unit 22 via their own heaters (and/or ozone or chemicals). In such case, the master heater would meet the needs of a first disinfection unit 26 for PD/HD/HDF/CRRT machine 30, while the delegate heater would be used to disinfect water purification unit 22.

Water purification unit 22 operates optimally at higher temperatures but does not require as precise a control because it has no direct patient connection. As seen in FIG. 7B, master heater is allowed to heat whenever needed. Rather than waiting for the delegate heater to finish heating before the master heater begins, system 10 commands the delegate heater to stop heating. The delegate heater then ceases to heat and the master heater resumes heating. When the master heater is finished, system 10 allows the delegate heater to heat again if needed, until such time as the master needs to heat again, causing system 10 to power the delegate heater down, and so on.

Method or algorithm 160 of FIG. 7B starts at oval 162 and at diamond 164 determines whether the master heater needs power. If so, algorithm 160 removes power from the delegate heater if it is being heated, as seen at block 166 and powers the master heater as seen at block 168 (e.g., for a PWM time segment). A loop between diamond 164, block 166 and block 168 continues until the master heater no longer needs power as determined at diamond 164. Algorithm 160 next determines whether the delegate heater needs power at diamond 170. If so, algorithm 160 powers the delegate heater at block 172 (e.g., for a PWM time segment). Instead of feeding back to diamond 170 to determine if the delegate heater still needs to be powered, method 160 returns to diamond 164 to determine if the mater heater needs power. If so, the loop between diamond 164, block 166 and block 168 is begun again and continues until the master heater no longer needs power as determined at diamond 164. Thus, the heating of the delegate heater is interrupted as seen at block 166. The loop between diamond 164, diamond 170 and block 172 continues until the delegate heater no longer needs power as determined at diamond 170. Method 160 of system 10 then determines if the system should be shut down at diamonded 174. If so, method 160 ends as seen at oval 176. If not, the entire method is begun again at diamond 164.

Figure 8:
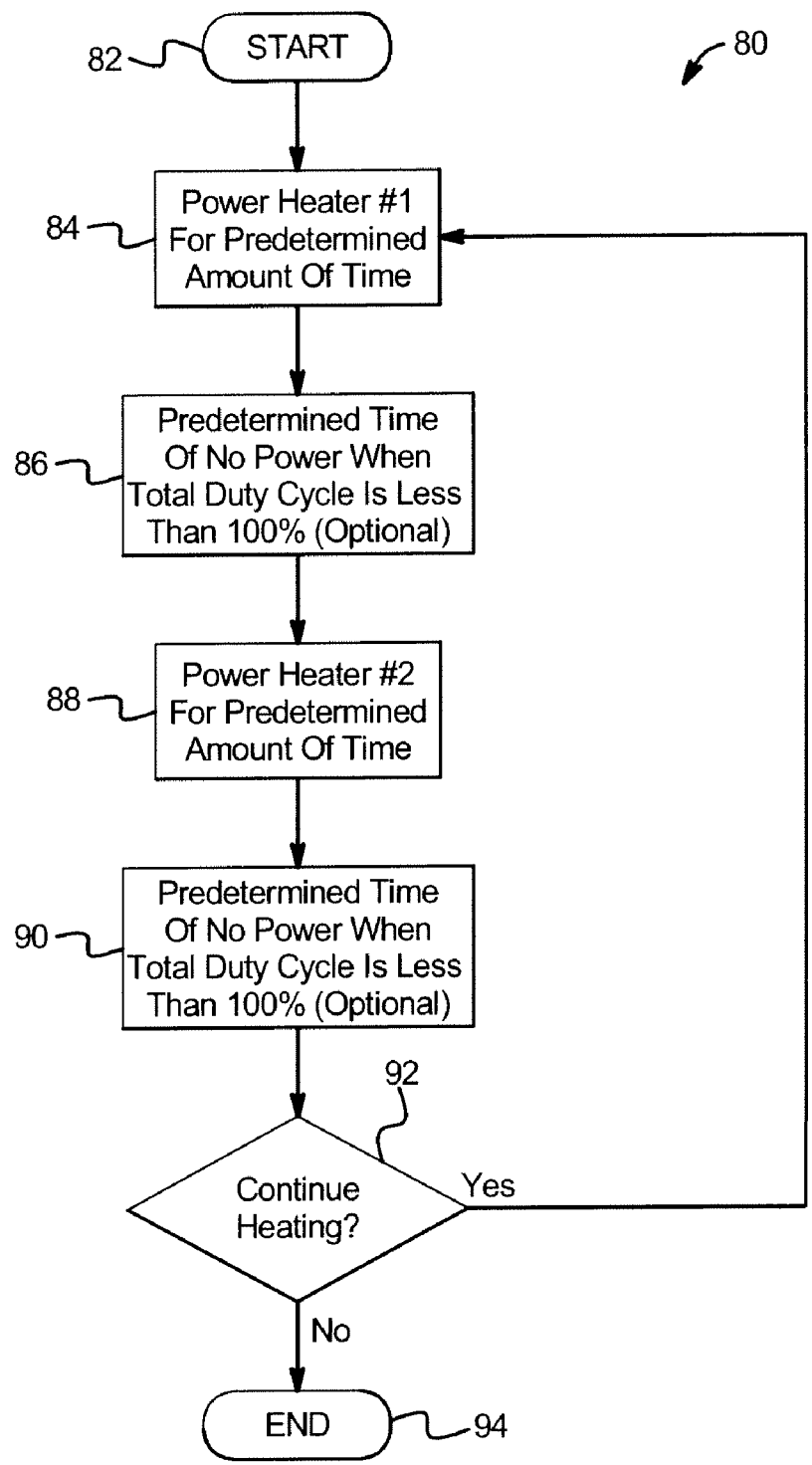
FIG. 8 is a logic flow diagram illustrating a further method or algorithm for powering dual heaters of a medical fluid system.

Referring now to FIG. 8, method or algorithm 80 illustrates a further alternative method or algorithm for controlling the duty cycles of first and second heaters of a medical fluid treatment, such as a dialysis treatment, so that total power draw at any given time does not exceed a maximum rated power draw for the patient's branch electrical system (residential or commercial). Method or algorithm 80 begins at oval 82, and a first heater of the medical fluid system is powered for a predetermined amount of time (according to its PWM sequence) as seen at block 84. If the total duty cycle of both heaters is less than one-hundred percent (e.g., the first heater has a duty cycle of fifty-nine percent on and the second heater has a duty cycle of forty percent), method or algorithm 80 can apportion some or all of the available off time and consume a predetermined amount of the off time (no power to either heater) at this point in method 80, as seen at block 86.

Method or algorithm 80 then powers a second heater of the medical fluid system for a predetermined amount of time (according to its PWM sequence) as seen at block 88. If the total duty cycle of both heaters is less than one-hundred percent, method or algorithm 80 can apportion some or all of the available off time and consume a predetermined amount of the off time (no power to either heater) at this point in method 80, as seen at block 90.

At diamond 92, method or algorithm 80 determines whether to continue heating (whether fluid heating is completed). If so, the steps taken at blocks 84 to 90 are repeated until heating is no longer required, as determined at diamond 92, at which time method or algorithm 80 ends, as seen at oval 94.

Methods or algorithms 60, 160 and 80 of FIGS. 7A, 7B and 8 are particularly well suited for instances in which the total duty cycle (combined duty cycles of first and second heaters) is less than or equal to one-hundred percent. That is, the percentage of time that the first heater is powered plus the percentage of time that the second heater is powered is less than or equal to one-hundred percent. In such case, methods or algorithms 60, 160 and 80 ensure that the heating of one heater does not overlap the heating of the second heater. Accordingly, the power or current drawn due to the heating of the medical fluid system is never greater than the full power or current drawn by either heater taken alone.

It should be appreciated that if three heaters (or more) combined for less than a total duty cycle of one hundred percent then method 80, for example, could be expanded to control three or more heaters without exceeding a branch line current or power limit.

Figure 9:
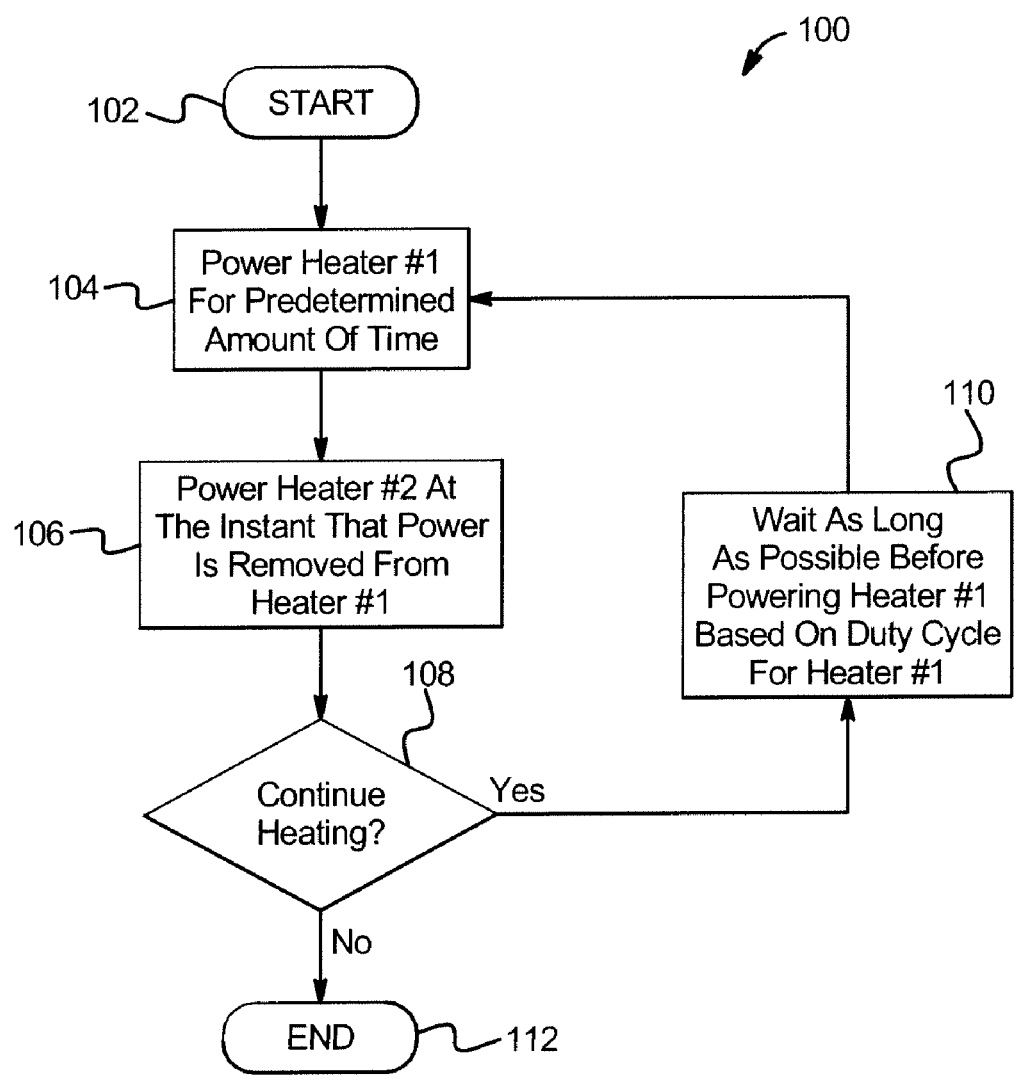
FIG. 9 is a logic flow diagram illustrating one method or algorithm for powering dual heaters of a medical fluid system when the two heaters will at certain times be powered simultaneously.

FIG. 9 illustrates a method or algorithm 100 which is employed when the total duty cycle of both heaters exceeds one-hundred percent. This method or algorithm attempts to minimize as much as possible the time that the two heaters have to be powered simultaneously. Method or algorithm 100 begins at oval 102 as illustrated. The first heater is powered for a predetermined amount of time, as seen at block 104. The second heater is powered at the instant that power is removed from the first heater, as seen at block 106. Thus, up to block 106, there is no overlap in heating. Method or algorithm 100 then determines whether the system is to continue heating, as determined at diamond 108. If so, method or algorithm 100 waits as long as possible before powering the first heater again based on the duty cycle for the first heater. The above loop continues until heating is discontinued, as determined at diamond 108, after which method or algorithm 100 ends, as seen at oval 112.

By waiting as long possible at block 110, method or algorithm 100 maximizes an opportunity that the duty cycle of the first heater due to a control algorithm for that heater may be lessened between sequential applications of power to the first heater. If the duty cycle of the first heater is diminished, method 100 can wait an additional amount of time before re-powering the first heater, minimizing any overlapping time that both heaters are powered.

Method or algorithm 100 may be modifies to satisfy a master/delegate relationship between the heaters. Here, the first or mater heater is powered as needed. The second or delegate heater is powered for as long as needed but only if the first, master heater is not being heated. Thus, the second, delegate heater may be "starved" of power for certain periods. Or, the method or algorithm may allow for a small amount of overlap, ensuring (i) the first, master heater receives as much power as needed and (ii) that the overlap does not exceed or overly exceed a current or power rating of the patient's or clinic's facility.

FIGS. 5 and 6 above show different embodiments for using a supplemental power source 14 in combination with branch power 12 to separate and dedicate first and second heaters to one of the power sources. For example, FIG. 5 shows branch power dedicated to the dialysate delivery heater, while supplemental power supply 14 is dedicated to the heater for the water purification unit. FIG. 6 shows an alternative embodiment in which branch power 12 is dedicated to the water purification heater, while supplemental power supply 14 is dedicated to the dialysate delivery heater.

Figure 10:
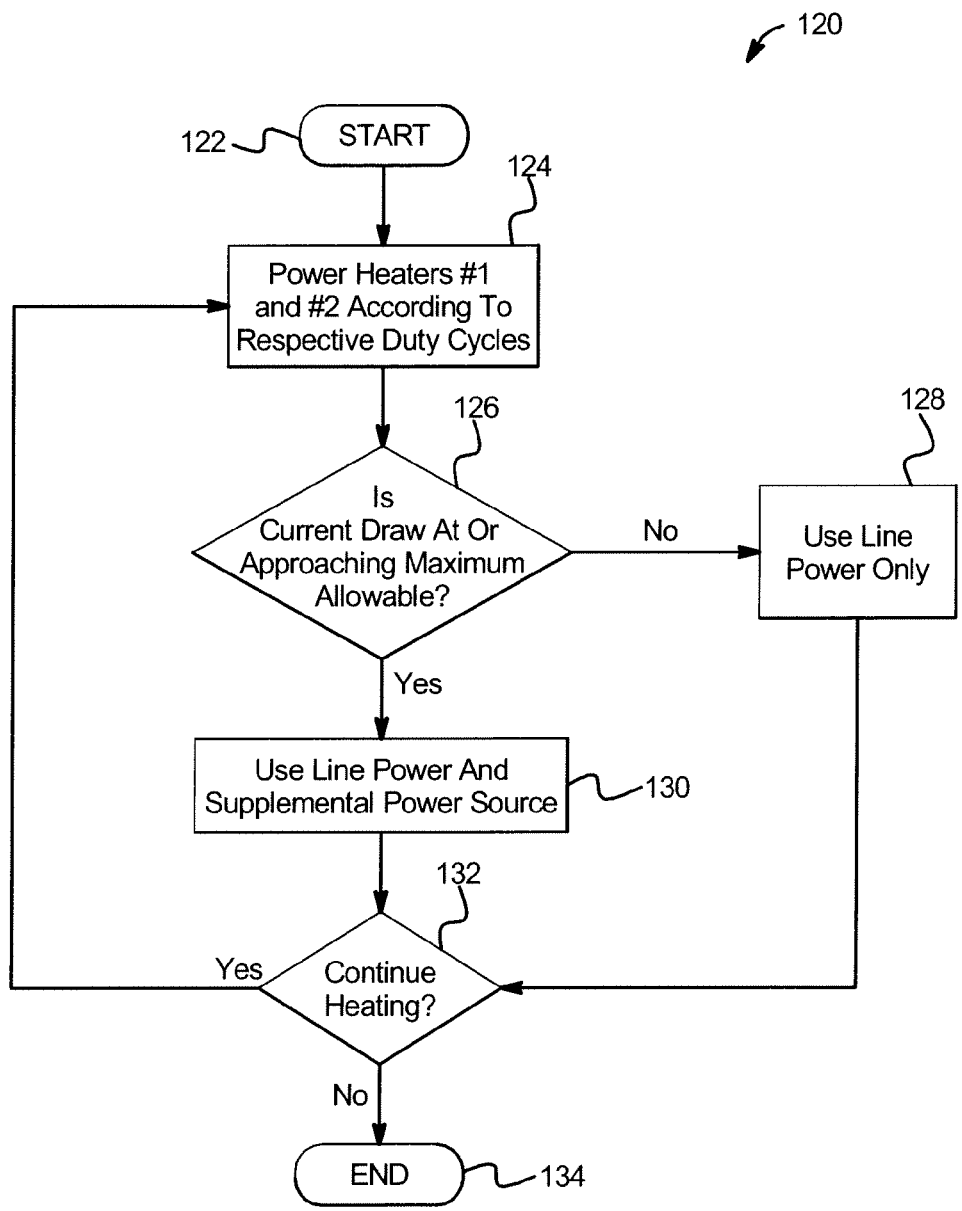
FIG. 10 is a logic flow diagram illustrating another method or algorithm for powering dual heaters of a medical fluid system when the two heaters will at certain times be powered simultaneously.

Referring how to FIG. 10, method or algorithm 120 illustrates an alternative embodiment for incorporating supplemental power supply 14 to ensure that the patient's branch power source is not overtaxed at a time that both heaters have to be powered simultaneously.

Method or algorithm 120 begins at oval 122. The first and second heaters are powered according to their respective duty cycles, as indicated at block 124. At diamond 126, method or algorithm 120 determines whether the current draw is at or approaching a maximum allowable current draw. For example, the method or algorithm 120 could determine at diamond 126 whether the current draw is at ninety-five percent of a maximum allowable current draw. If the current draw is not at or approaching the maximum allowable, method or algorithm 120 uses only line power supply 12, as seen at block 128. If the current draw is at or approaching a maximum as determined at diamond 126, method or algorithm 120 uses the line power 12 and supplemental power source 14, as seen at block 130. Here, the branch 12 and supplemental power 14 sources can be distributed according to any suitable configuration shown in FIGS. 3 to 6.

At diamond 132, method or algorithm 120 determines whether the system is to continue heating. If not, method or algorithm 120 ends, as seen at oval 134. If so, the steps just described are repeated until heating is completed.

Figure 11:
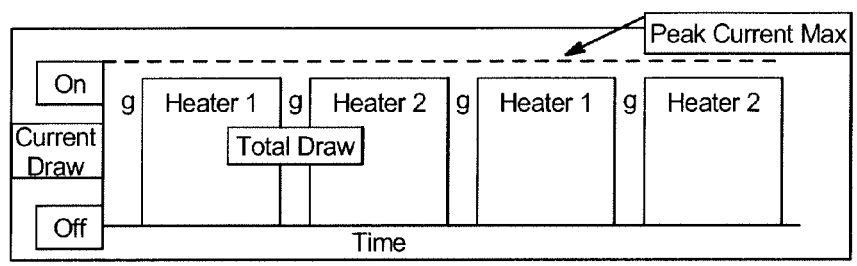
FIG. 11 is a graph of current draw versus time for dual heaters of a medical fluid system when the total duty cycle for both heaters is less than one-hundred percent.

Referring now to FIG. 11, a graph of current draw verses time shows graphically how the power is distributed to the first and second heaters in a situation when the total duty cycle of both heaters is less than one-hundred percent. Here, a gap g exists in time between each power-on sequence for either the first and second heaters. Here, the total time that both heaters are on is less than one-hundred percent of the time. Accordingly, the powering of the first and second heaters is spaced apart as much as possible, so that power draw from the line 12 or branch 14 power supplies has a rest period before the powering of either heater.

In an alternative embodiment, the second heater is powered at the instant the first heater is switched de-powered, creating a larger time gap g between the time that the second heater is powered and the time that the first heater is powered.

Figure 12:
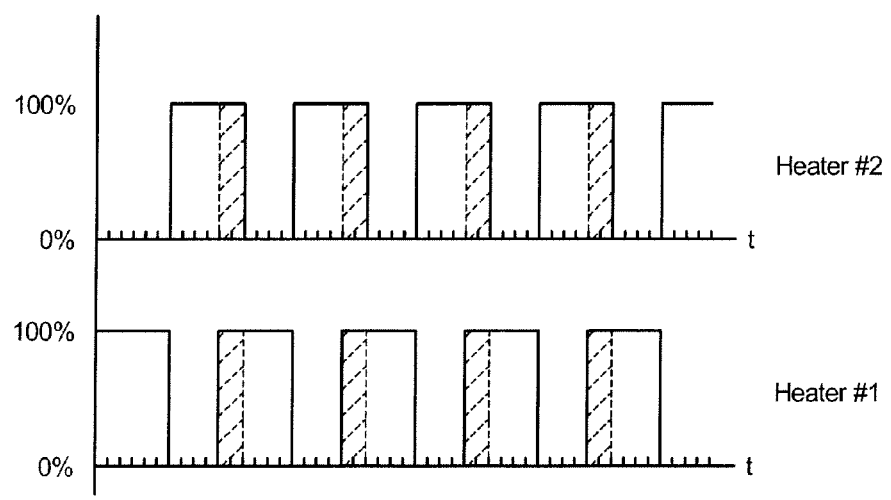
FIG. 12 is a graph of current draw versus time for dual heaters of a medical fluid system when the total duty cycle for both heaters is more than one-hundred percent.

Referring now to FIG. 12, algorithm 100 of FIG. 9 is illustrated graphically. Here, as an example, both heaters have an individual sixty percent duty cycle, meaning that each heater needs to be powered for sixty percent of the total time at full power. Thus beginning at every ten time increments and continuing for two time increments, the total power drawn is the sum of the power needed by both the first and second heaters. Here, the second heater is powered at the instant that power is removed from the first heater. In the example, and assuming the duty cycles of the heaters stay the same, the system waits four time periods before re-powering the first heater, which is the maximum allowable time that the system can wait before re-powering the first heater according to the existing sixty percent duty cycle of the first heater.

If either the duty cycle of the first or second heaters is lessened during this waiting period, the overlap in the heating of both heaters simultaneously can be lessened. For example, if after the first six time increments, the duty cycle of the second heater is reduced to fifty percent, waiting until ten time increments to re-power the first heater will allow the overlap in time both heaters are being heated simultaneously to a single time increment. In another example, if the duty cycle of the first heater at any time between time increment six and time increment ten lessens, e.g., changes to fifty percent, then the system can wait until time period eleven before re-powering the first heater, thus reducing or possibly eliminating (e.g., if duty cycle is decreased to forty percent) the overlap between time period ten and time period twelve.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   a first fluid heater;
   a second fluid heater;
   a logic implementer configured to synchronize the duty cycles of the first and second heaters so that the first and second heaters are powered simultaneously as little as possible if a collective duty cycle of the first and second heaters is greater then one-hundred percent.

2. The dialysis system of claim 1, the logic implementer configured to de-power one of the first and second fluid heaters at the instant that the other of the first and second fluid heaters is powered.

3. The dialysis system of claim 1, the logic implementer further configured to disallow the first and second fluid heaters from being powered simultaneously if a collective duty cycle of the first and second fluid heaters is less than one-hundred percent.

4. The dialysis system of claim 1, the first fluid heater a master fluid heater that is powered when needed, the second fluid heater a delegate fluid heater that is powered only when the first, master fluid heater is not being powered.

5. The dialysis system of claim 1, wherein at least one of the first and second fluid heaters is an in-line fluid heater.

6. The dialysis system of claim 1, the logic implementer configured to power the heaters using pulse width modulation.

7. The dialysis system of claim 1, the first fluid heater configured to heat a first fluid and the second fluid heater configured to heat a second, different fluid.

8. The dialysis system of claim 1, the first fluid heater configured to operate with a dialysis fluid preparation unit and the second fluid heater configured to operate with a dialysis fluid delivery unit.

9. A fluid heater method for a dialysis therapy comprising:
   synchronizing first and second duty cycles for first and second fluid heaters used for the dialysis therapy so that the first and second heaters are powered simultaneously as little as possible when a collective duty cycle for the first and second heaters exceeds one-hundred percent.

* * * * *